United States Patent [19]

Schaumann et al.

[11] 4,353,895
[45] Oct. 12, 1982

[54] CARDENOLIDE-BIS-DIGITOXOSIDE ALKYL COMPOUNDS, PHARMACEUTICAL COMPOSITIONS AND METHOD OF USE

[75] Inventors: Wolfgang Schaumann, Heidelberg; Fritz Kaiser, Lampertheim; Wolfgang Voigtländer, Weinheim; Edgar Hoyer; Klaus Koch, both of Mannheim, all of Fed. Rep. of Germany

[73] Assignee: Boehringer Mannheim GmbH, Mannheim, Fed. Rep. of Germany

[21] Appl. No.: 288,442

[22] Filed: Jul. 30, 1981

[30] Foreign Application Priority Data

Sep. 13, 1980 [DE] Fed. Rep. of Germany ....... 3034658

[51] Int. Cl.$^3$ ...................... A61K 31/705; C07J 19/00
[52] U.S. Cl. ........................................ 424/182; 536/7
[58] Field of Search .......................... 424/182; 536/7

[56] References Cited

U.S. PATENT DOCUMENTS 3,458,628 7/1969 Kaiser et al. ............................. 536/7
3,462,528 8/1969 Voigtlander et al. ................... 536/7
3,909,357 9/1975 Reinhard et al. ....................... 536/7

Primary Examiner—Johnnie R. Brown

Attorney, Agent, or Firm—Sprung, Horn, Kramer & Woods

[57] ABSTRACT

Cardioactive cardenolide-bis-digitoxosides of the formula

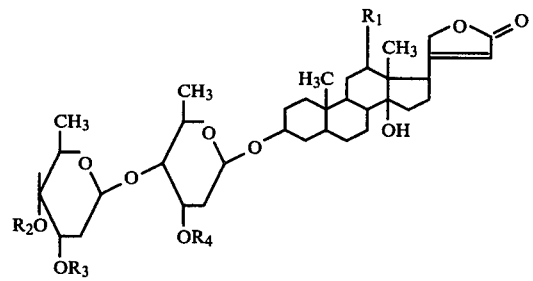

in which $R_1$ is a hydrogen atom, a hydroxyl group or an acyloxy radical containing up to 3 carbon atoms, and $R_2$, $R_3$ and $R_4$ each independently is a hydrogen atom, an acyl radical containing up to 3 carbon atoms, with the proviso that the compound contains at least one alkyl radical. The compounds exhibit desirable rates of excretion, primarily extrarenally.

8 Claims, No Drawings

CARDENOLIDE-BIS-DIGITOXOSIDE ALKYL COMPOUNDS, PHARMACEUTICAL COMPOSITIONS AND METHOD OF USE

The present invention is concerned with new cardenolide bis-digitoxosides, processes for the preparation thereof and pharmaceutical compositions containing them.

The new cardenolide bis-digitoxosides according to the present invention are compounds of the general formula:

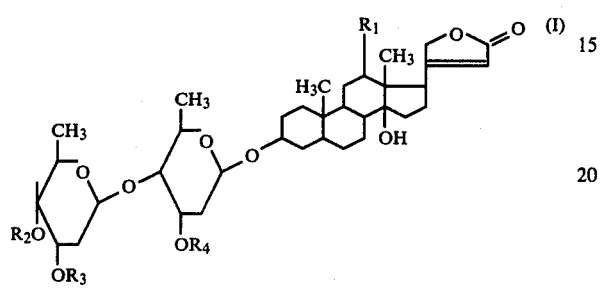

wherein $R_1$ is a hydrogen atom, a hydroxyl group or an acyloxy radical containing up to 3 carbon atoms and $R_2$, $R_3$ and $R_4$, which can be the same or different, are hydrogen atoms, acyl radicals containing up to 3 carbon atoms or alkyl radicals containing up to 3 carbon atoms, with the proviso that these compounds contain at least one alkyl radical.

We have found that the compounds of general formula (I) are useful for the treatment of cardiac insufficiency.

The digitalis glycosides digitoxin and digoxin, as well as derivatives thereof, for example acetyldigoxin and methyldigoxin, which are mainly used for the therapy of cardiac insufficiency, still leave something to be desired in the breadth of their possibilities of use.

Digoxin and its derivatives are preponderantly excreted through the kidneys and can, therefore, lead to intoxication in patients with impaired kidney function.

Digitoxin, on the other hand, is excreted extrarenally but, of the above-mentioned compounds, is the one with the longest period of residence in the organism, for which reason, if intoxidation occurs, for example in the case of overdosing, this will only subside again very slowly.

We have now found that the carbenolide bisdigitoxides according to the present invention are excreted much more quickly than digitoxin—roughly the same as digoxin—but slower than unsubstituted bis-digitoxosides which are only transitoryly effective. In particular the excretion from the organism takes place mainly extrarenally and thus they are outstanding suitable for the therapy of cardiac insufficiency accompanied with impaired kidney function.

The new cardenolide-bis-digitoxosides according to the present invention can be prepared in the following manner:

(a) compounds of the general formula:

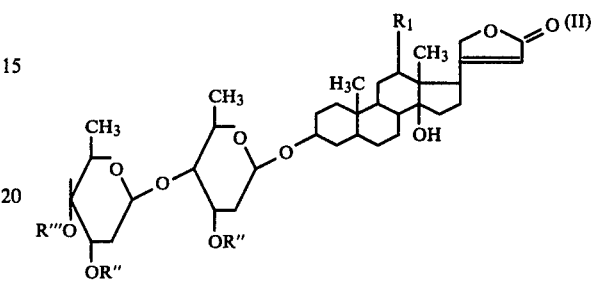

in which $R_1$ is a hydrogen atom, a hydroxyl group or an acyloxy radical, $R'$ is a hydrogen atom or an acyl or alkyl radical and $R''$ and $R'''$, which can be the same or different, are hydrogen atoms or alkyl or acyl radicals or together represent a cyclic acetal or ketal, at least one of the symbols $R'$, $R''$ and $R'''$ being a hydrogen atom, are acylated or alkylated one or more times in known manner with appropriate acylation or alkylation agents, whereupon, if desired, one or more acyl, acetal or ketal groups are split off by selective hydrolysis, whereupon, if desired, a free hydroxyl group is acylated or alkylated with a further acylation or alkylation agent; or (b) a compound of the general formula:

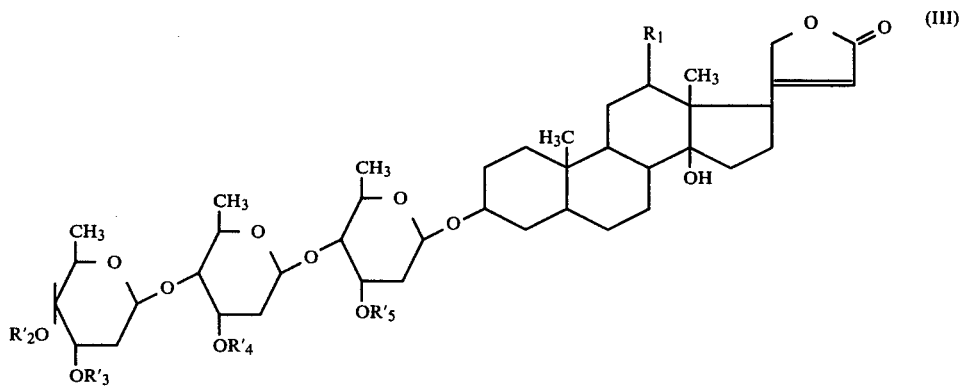

in which $R_1$ is a hydrogen atom, a hydroxyl group or an acyloxy radical, $R'_2$ and $R'_3$ together represent a cyclic acetal or ketal with 2 to 5 carbon atoms or each represents an acyl racical and $R'_4$ and $R'_5$, which can be the same or different, each represent alkyl radicals containing up to 3 carbon atoms or acyl radicals, are reacted by selective hydrolysis of the acyl, acetal or ketal groups $R'_2$ and $R'_3$ and subsequent oxidative splitting off of the terminal digitoxose, whereupon, if desired, one or more free hydroxyl groups are converted with appropriate acylation and/or alkylation agents into acyloxy and/or alkoxy radicals.

For the alkylation of the compounds of general formulae (II) and (III), it is preferred to use the alkylation process described in Federal Republic of Germany Pat. Nos. 1,961,034 and 2,233,147 (Example 1), which employed graduated amounts of a dialkylsulphate in the presence of strontium hydroxide or of barium hydroxide or of aluminium isopropylate and aluminium oxide in an inert solvent, although other conventional alkylation agents, for example alkyl halides, alkyl tosylates and alkyl mesylates can also be used (see Federal Republic of Germany Pat. No. 2,734,401).

The acylation of the compounds can be carried out, for example, by the process described in Arzneium, Forsch., 15, 481, Federal Republic of Germany Pat. No. 1,063,160 and Pharm. Bull., 5, 171/1955, using graduated amounts of acid anhydrides in pyridine or dimethylformamide, optionally with subsequent separation of the acylation products by multiplicative partitioning or by chromatographic methods, acylation thereby being preferably in the 10′-position although, in the case of comparatively long reaction times, completely acylated derivatives are also obtained.

Furthermore, the acylation can be carried out by the method described in Federal Republic of Germany Pat. No. 2,206,737 using dialkylacetamidedialkyl acetals or by using ortho esters according to Federal Republic of Germany Pat. No. 2,010,422 in an inert solvent, products acylated in the 9′-position preferably being obtained.

According to the method described in Federal Republic of Germany Pat. No. 2,110,646, the reaction of compounds (II) with acylation agents in the presence of a tertiary amine preponderantly give rise to 9′,10′-diacyl derivatives.

Finally 12-acyl-digoxigenin-bis-digitoxosides can be obtained by the method of Federal Republic of Germany Pat. No. 2,126,305 by peracylation and partial saponification.

Ketal groups are preferably split off in weakly acidic solutions in water or in aqueous alcohols.

Acyl radicals and especially the 9′,10′- and 15′,16′-substituents are preferably split off in weakly basic solutions, for example in aqueous bicarbonate solutions. Acid anhydrides or mixed acid anhydrides are preferably used as acylation agents because of the simplicity with which they can be used and because of their low cost but appropriate acid chlorides, imidazolides and other known acylating agents can be used with equal success.

The end products are worked up and purified by the conventional methods, using multiplicative partitioning or chromatography and crystallisation.

The identity and purity of the compounds obtained were examined by thin layer chromatography. For this purpose, use was made of TLC finished plates (Merck silica gel 60/F 254; impregnation with 20% formamide in acetone) and developing with the elution agent xylene-methyl ethyl ketone (2:3 v/v)+5% formamide. The final chromatograms were sprayed with trichloroacetic acid-chloramine reagent and the substances determined by their fluorescence in longwave ultraviolet light ($\lambda = 360$ nm). The running length (R) in the chromatogram was, in each case, referred to a simultaneously run standard. In this case, $R_D$ means the R value referred to the running length of the digitoxigenin-bis-digitoxoside and $R_{DG}$ means the R value referred to the running length of the digoxigenin-bis-digitoxoside.

The cardenolide glycosides according to the present invention are effective in the same range of dosage as usual heart glycosides, as for example digoxin or digitoxin, and can be administered one to four times daily in individual dosages of 0.050 to 0.250 mg. Administration is preferably orally but parenteral administration is also possible.

For oral administration, it is preferred to use tablets or hard or soft gelatine capsules. For individual administration of the dosages, for example in the case of children, the composition is preferably in the form of a liquid. For emergency and stationary treatment, administration can be by means of the injection of appropriate solutions.

For the preparation of tablets or hard gelatine capsules for oral administration, the active material is homogeneously mixed with conventional adjuvants, for example lactose and starch, whereby, because of the small individual dosages, it is preferred to prepare a pre-mixture. The active material-adjuvant mixture can, by selection of appropriate adjuvants, be filled into the capsules as a dry powder mass or, by granulation with the use of binding agents, such as starch paste or polyvinylpyrrolidone, can be pressed as a granulate to give tablets, with the further admixture of conventional disintegration agents and lubricating agents.

Carrier materials for soft gelatine tablets can be the conventional glycerol fatty acid esters but also polyethylene glycols as solvents for the active material. As solvent for liquid or ampoule forms, use can be made of, for example, ethanol or polyhydroxy alcohols in measured mixtures.

The following Examples are given for the purpose of illustrating the present invention:

EXAMPLE 1

9′-Methyldigitoxigenin-bis-digitoxoside 4 g. Aluminium isopropylate in 20 ml. dimethylformamide and 3.2 ml. methyl iodide are stirred for 5 hours at ambient temperature, then mixed with 4 g. digitoxigenin-bis-digitoxoside and further stirred for 3 days at ambient temperature. Subsequently, the reaction mixture is diluted with 320 ml. chloroform, suction filtered through kieselguhr, then washed with chloroform and the chloroform solution evaporated in a vacuum. The residue is dissolved in 120 ml. methanol and 180 ml. 10% acetic acid, shaken up with chloroform and the chloroform phase washed with 5% aqueous sodium bicarbonate solution, dried with anhydrous sodium sulphate and evaporated. The crude product is dissolved in ethyl acetate and fractionated over 200 g. aluminium oxide (+5% water) using ethyl acetate-chloroform. The evaporation residue of the chloroform fraction gives, after crystallisation from aqueous acetone and aqueous ethanol, 2.1 g. 9′-methyldigitoxigenin-bis-digitoxoside; m.p. 145°–148° C.; $R_D$: 1.23.

EXAMPLE 2

10′-Methyldigitoxigenin-bis-digitoxoside 2 g. Digitoxigenin-bis-digitoxoside, dissolved in 14 ml. dimethylformamide and 14 ml. toluene, are, after the addition of 0.68 g. aluminium oxide (Merck according to Brockmann), 1.12 g. strontium hydroxide octahydrate and 2.0 ml. dimethyl sulphate in 22 ml. toluene, stirred for 4 hours at ambient temperature. The reaction mixture is subsequently diluted with 40 ml. chloroform, filtered over 12 g. kieselguhr, washed with 40 ml. chloroform and 2.6 ml. morpholine added thereto, left to stand for 30 minutes and then, after the addition of 15 ml. water, stirred for 15 minutes. The chloroform phase is separated off, again stirred for 15 minutes with 10 ml. water and the chloroform phase evaporated in a vacuum. The crude product is dissolved in ethyl acetate and fractionated over 110 g. aluminium oxide (+5% water) with ethyl acetate, chloroform and chloroform-methanol (1:1 v/v). The evaporation residue of the chloroform fraction gives, after crystallisation from chloroform-diethyl ether and aqueous ethanol, 1.45 g. 10′-methyldigitoxigenin-bis-digitoxoside; m.p. 197°–203° C.; $R_D$: 1.24.

EXAMPLE 3

10′-Ethyldigitoxigenin-bis-digitoxoside 2 g. Digitoxigenin-bis-digitoxoside, dissolved in 16 ml. dimethylformamide, are, after the addition of 1.16 g. barium hydroxide octahydrate, 392 mg. barium oxide and 1.68 ml. diethyl sulphate, stirred for 6 hours at 30° to 35° C., while passing over nitrogen. The reaction mixture is subsequently diluted with 80 ml. chloroform, filtered over kieselguhr, washed with 40 ml. chloroform and 12 ml. morpholine added thereto, then left to stand for 30 minutes, shaken up with 20 ml. water and the chloroform phase evaporated in a vacuum. The crude product is separated with cyclohexane-ethyl acetate (3:1 v/v) over a column of cellulose (impregnated with formamide). The evaporation residue of the chromatographically uniform fractions gives, after crystallisation from ethyl acetate, 920 mg. 10′-ethyldigitoxigenin-bis-digitoxoside; m.p. 213°–217° C.; $R_D$: 1.33.

EXAMPLE 4

10′-n-Propyldigitoxigenin-bis-digitoxoside 2 g. Digitoxigenin-bis-digitoxoside, dissolved in 16 ml. dimethylformamide, are reacted with 1.16 g. barium hydroxide, 392 mg. barium oxide and 1.68 ml. di-n-propyl sulphate and worked up in the manner described in Example 3. The crude product is separated with heptane-methyl ethyl ketone (3:1 v/v) over a cellulose column (impregnated with formamide). The evaporation residue of the chromatographically uniform fractions gives, after crystallisation from ethyl acetate, 820 mg. 10′-n-propyldigitoxigenin-bis-digitoxoside; m.p. 228°–232° C.; $R_D$: 1.38.

EXAMPLE 5

9′,10′-Dimethyldigitoxigenin-bis-digitoxoside.

4 g. Digitoxigenin-bis-digitoxoside, dissolved in 48 ml. dimethyl acetamide, are, after the addition of 11.2 g. barium hydroxide octahydrate and 14.4 ml. dimethyl sulphate, stirred for 4 hours at ambient temperature. The reaction mixture is subsequently diluted with 300 ml. chloroform, filtered over kieselguhr, washed with 300 ml. chloroform and 20 ml. morpholine added thereto, then left to stand for 30 minutes, after the addition of 90 ml. water stirred for 15 minutes, the chloroform phase is separated off, again stirred for 15 minures with 60 ml. water and the chloroform phase evaporated in a vacuum. The crude product is separated with cyclohexane-ethyl acetate (4:1 v/v) over a cellulose column (impregnated with formamide). The evaporation residue of the chromatographically uniform fractions gives, after crystallisation from ethyl acetate, 1.3 g. 9′,10′-dimethyldigitoxigenin-bis-digitoxoside; m.p. 225°–228° C.; $R_D$: 1.40.

EXAMPLE 6

3′,9′,10′-Trimethyldigitoxigenin-bis-digitoxoside 3 g. Digitoxigenin-bis-digitoxoside, dissolved in 36 ml. dimethyl acetamide, are, after the addition of 8.4 g. barium hydroxide octahydrate and 10.8 ml. dimethyl sulphate, reacted and worked up in the manner described in Example 5. The crude product is separated with heptane-methyl ethyl ketone (3:1 v/v) over a cellulose column (impregnated with formamide). The evaporation residue of the chromatographically uniform fractions gives, after crystallisation from chloroformmethanol-petroleum ether, 1.06 g. 3′,9′,10′-trimethyldigitoxigenin-bis-digitoxoside; m.p. 91°–95° C.; $R_D$: 1.48.

EXAMPLE 7

3′-Methyldigitoxigenin-bis-digitoxoside 10 g. Digitoxigenin-bis-digitoxoside, dissolved in 100 ml. chloroform-methanol (1:1 v/v), are, after the addition of 260 ml. anhydrous acetone, 20 ml. 2,2-dimethoxypropane and 30 mg. p-toluenesulphonic acid, stirred for 2 hours at ambient temperature, then diluted with 400 ml. 5% aqueous sodium bicarbonate solution and shaken out with chloroform. After washing with water and drying with anhydrous sodium sulphate, the chloroform phase is evaporated in a vacuum. The residue is dissolved in 400 ml. carbon tetrachloride-chloroform (4:1 v/v) and fractionated over 100 g. aluminium oxide (Merck according to Brockmann). The residue from the evaporated carbon tetrachloride-chloroform fraction gives, after crystallisation from diethyl ether, 6.1 g. 9′,10′-isopropylidene-digitoxigenin-bis-digitoxoside. 6 g. 9′,10′-Isopropylidenedigitoxigenin-bis-digitoxoside, dissolved in 45 ml. dimethyl acetamide, are, after the addition of 21 g. barium hydroxide octahydrate and 13 ml. dimethyl sulphate, reacted and worked up as described in Example 5. In order to split off the isopropylidene group, the crude product (6.1 g.) is dissolved in 360 ml. glacial acetic acid-water (1:1 v/v), left to stand for 16 hours at ambient temperature, diluted with 1.5 liters water, shaken out with chloroform and evaporated in a vacuum. The crude 3′-methyldigitoxigenin-bis-digitoxoside obtained is purified with cyclohexane-ethyl acetate (3:1 v/v) over a cellulose column (impregnated with formamide). The evaporation residue of the chromatographically uniform fractions gives, after crystallisation from ethyl acetate, 1.1 g. 3′-methyldigitoxigenin-bis-digitoxoside; m.p. 228°–233° C.; $R_D$: 1.17.

EXAMPLE 8

3′,9′-Dimethyldigitoxigenin-bis-digitoxoside 5 g. Isopropylidenedigitoxin, dissolved in 37 ml. dimethyl acetamide, are, after the addition of 17 g. barium hydroxide octahydrate and 11 ml. dimethyl sulphate, stirred for 1.5 hours at ambient temperature and then worked up as described in Example 5. The crude product (3.4 g.) is, in order to split off the isopropylidene group, dissolved in 210 ml. glacial acetic acid-water (1:1 v/v), left to stand for 16 hours at ambient temperature, diluted with 750 ml. water, shaken out with chloroform and evaporated in a vacuum. The crude 3′,9′-dimethyldigitoxin obtained is purified with cyclohexane-ethyl acetate (4:1 v/v) over a cellulose column (impregnated with formamide). Evaporation of the chromatographically uniform fractions gives 700 mg. pure 3',9'-dimethyldigitoxin.

In order to split off the terminal digitoxose, the 3',9'-dimethyldigitoxin is dissolved in 3.7 ml. chloroform and 11 ml. methanol, mixed dropwise, while stirring at ambient temperature, within the course of 30 minutes, with 2.7 ml. 10% aqueous sodium periodate solution, stirred for 1.5 hours at ambient temperature and filtered. The filtrate is diluted with water, shaken out with chloroform and the chloroform phase is washed with water, dried with anhydrous sodium sulphate and evaporated in a vacuum. The crude product is dissolved in 15 ml. 95% methanol and, after the addition of 75 mg. sodium borohydride, stirred for 1 hour at ambient temperature, shaken out with chloroform and the chloroform phases are washed with water, dried with anhydrous sodium sulphate and evaporated in a vacuum. The residue (0.6 g.) is dissolved in 15 ml. methanol, stirred for 3 hours at ambient temperature with 2.7 ml. 0.05 N hydrochloric acid, neutralised with 5% aqueous sodium bicarbonate solution, diluted with 15 ml. water, shaken out with chloroform and the chloroform phases are washed with water, dried with anhydrous sodium sulphate and evaporated in a vacuum. The residue, after crystallisation from diethyl ether-petroleum ether gives 520 mg. 3',9'-dimethyldigitoxigenin-bis-digitoxoside; m.p. 111°–115° C.; $R_D$: 1.25.

EXAMPLE 9

9'-Methyldigoxigenin-bis-digitoxoside.

4 g. Aluminium isopropylate in 20 ml. dimethylformamide are reacted with 3.2 ml. methyl iodide and 4 g. digoxigenin-bis-digitoxoside and worked up as described in Example 1. The crude product is dissolved in chloroform and fractionated over 30 g. aluminium oxide (Merck according to Brockmann) with chloroform and chloroform-methanol (1:1 v/v). The evaporation residue of the chloroform fraction gives, after crystallisation from aqueous ethanol and ethyl acetate, 2.34 g. 9'-methyldigoxigenin-bis-digitoxoside; m.p. 223°–226° C.; $R_{DG}$: 2.62.

EXAMPLE 10

10'-Methyldigoxigenin-bis-digitoxoside 2 g. Digoxigenin-bis-digitoxoside, dissolved in 14 ml. dimethylformamide and 14 ml. toluene, are reacted and worked up as described in Example 2. The crude product is subjected to a multiplicative partitioning with the phase mixture chloroform-carbon tetrachloridemethanol-water (1:1:1:1 v/v/v/v). The evaporated organic phase is then subjected to multiplicative partitioning with the phase mixture carbon tetrachloride-ethyl acetate-methanol-water (3:1:2:2 v/v/v/v). From the aqueous phase, there is obtained, after shaking out with chloroform, evaporating in a vacuum and crystallising the residue from aqueous methanol, 1.48 g. 10'-methyldigoxigenin-bis-digitoxoside; m.p. 154°–157° C.; $R_{DG}$: 2.63.

EXAMPLE 11

10'-Ethyldigoxigenin-bis-digitoxoside 2 g. Digoxigenin-bis-digitoxoside, dissolved in 16 ml. dimethylformamide, are reacted and worked up as described in Example 3. The crude product is separated with cyclohexane-ethyl acetate (1:1 v/v) over a cellulose column (impregnated with formamide). The evaporation residue of the chromatographically uniform fractions gives, after crystallisation from acetone-diethyl ether, 860 mg. 10'-ethyldigoxigenin-bis-digitoxoside; m.p. 232°–236° C.; $R_{DG}$: 3.12.

EXAMPLE 12

10'-n-Propyldigoxigenin-bis-digitoxoside 2 g. Digoxigenin-bis-digitoxoside, dissolved in 16 ml. dimethylformamide, are reacted with 1.16 g. barium hydroxide, 392 mg. barium oxide and 1.68 ml. di-n-propyl sulphate and worked up as described in Example 3. The crude product is separated with cyclohexane-ethyl acetate (2:1 v/v) over a cellulose column (impregnated with formamide). The evaporation residue of the chromatographically uniform fractions gives, after crystallisation from acetone-diethyl ether, 760 mg. 10'-n-propyldigoxigenin-bis-digitoxoside; m.p. 248°–251° C.; $R_{DG}$: 3.62.

EXAMPLE 13

9',10'-Dimethyldigoxigenin-bis-digitoxoside 4 g. Digoxigenin-bis-digitoxoside, dissolved in 48 ml. dimethyl acetamide, are reacted and worked up as described in Example 5. The crude product is separated with cyclohexane-ethyl acetate (3:1 v/v) over a cellulose column (impregnated with formamide). The evaporation residue of the chromatographically uniform fractions gives, after crystallisation from acetone, 1.74 g. 9',10'-dimethyldigoxigenin-bis-digitoxoside; m.p. 133°–137° C.; $R_{DG}$: 3.62.

EXAMPLE 14

3',9',10'-Trimethyldigoxigenin-bis-digitoxoside 3 g. Digoxigenin-bis-digitoxoside, dissolved in 36 ml. dimethyl acetamide, are, after the addition of 8.4 g. barium hydroxide octahydrate and 10.8 ml. dimethyl sulphate, reacted and worked up as described in Example 5. The crude product is separated with cyclohexane-ethyl acetate (3:1 v/v) over a cellulose column (impregnated with formamide). The chromatographically uniform fractions give, after crystallisation from acetone-diethyl ether-petroleum ether, 920 mg. 3',9',10'-trimethyldigoxigenin-bis-digitoxoside; m.p. 120°–122° C.; $R_{DG}$: 4.12.

EXAMPLE 15

9'-Acetyl-10'-methyldigoxigenin-bis-digitoxoside.

2 g. 10'-Methyldigoxigenin-bis-digitoxoside, dissolved in 20 ml. dimethylformamide, are, after the addition of 400 mg. triethylenediamine and 0.4 ml. acetic anhydride, left to stand for 24 hours at ambient temperature. The reaction mixture is subsequently diluted with 200 ml. water, shaken out with chloroform and the chloroform phases, after washing with 2 N sulphuric acid, aqueous sodium carbonate solution and water, evaporated in a vacuum. The crude product is separated with cyclohexane-ethyl acetate (2:1 v/v) over a cellulose column (impregnated with formamide). The evaporation residue of the chromatographically uniform fractions gives, after crystallisation from diethyl ether-petroleum ether, 530 mg. 9'-acetyl-10'-methyldigoxigenin-bis-digitoxoside; m.p. 141°–145° C.; $R_{DG}$: 4.20.

EXAMPLE 16

12-Acetyl-10'-methyldigoxigenin-bis-digitoxoside 4 g. 10'-Methyldigoxigenin-bis-digitoxoside, dissolved in 20 ml. pyridine, are, after the addition of 520 mg. acetic anhydride, left to stand for 24 hours at ambient temperature, then diluted with water, shaken out with chloroform and the chloroform phases, after washing with 2 N sulphuric acid and water, evaporated in a vacuum. The crude product is fractionated with cyclohexane-ethyl acetate (3:1 v/v) over a cellulose column (impregnated with formamide). The evaporation residue of the chromatographically uniform fractions gives, after crystallisation from acetone-diethyl ether-petroleum ether, 1.43 g. 12-acetyl-10'-methyldigoxigenin-bis-digitoxoside; m.p. 204°–208° C.; $R_{DG}$: 4.29.

EXAMPLE 17

3',9'-Diacetyl-10'-methyldigitoxigenin-bis-digitoxoside.

1 g. 10'-Methyldigitoxigenin-bis-digitoxoside, dissolved in 10 ml. pyridine, is, after the addition of 5 ml. acetic anhydride and 100 mg. 4-dimethylaminopyridine, left to stand for 2 hours at ambient temperature, then diluted with water, shaken out with chloroform and the chloroform phases, after washing with 2 N sulphuric acid and water, filtered over aluminium oxide and evaporated in a vacuum. The crude product gives, after crystallisation from diethyl ether-petroleum ether, 960 mg. 3',9'-diacetyl-10'-methyldigitoxigenin-bis-digitoxoside; m.p. 116°–120° C.; $R_{DG}$: 1.40.

EXAMPLE 18

Tablets

| | | |
|---|---|---|
| Ia | 10'-methyldigitoxigenin-bis-digitoxoside | 0.050 parts by wt. |
| | lactose | 45.450 parts by wt. |
| | corn starch | 10.000 parts by wt. |
| Ib | 10'-methyldigitoxigenin-bis-digitoxoside | 0.250 parts by wt. |
| | lactose | 45.250 parts by wt. |
| | corn starch | 10.000 parts by wt. |
| II | polyvinylpyrrolidone | 2.000 parts by wt. |
| III | sodium carboxymethyl starch | 2.000 parts by wt. |
| | microcrystalline cellulose | 15.000 parts by wt. |
| | magnesium stearate | 0.500 parts by wt. |

Preparation: A mixture of Ia respective Ib is granulated with an aqueous solution of II, dried and sieved. The granulate is mixed with the sustances of III. The tabletting mass thus obtained is tabletted to give 75 mg. tablets.

EXAMPLE 19

Liquid composition

| | | |
|---|---|---|
| | 9',10'-dimethyldigitoxigenin-bis-digitoxoside | 7.5 mg. |
| | glycerol | 3.0 ml. |
| | ethanol | ad 10.0 ml. |

Preparation: The active substance is dissolved in part of the ethanol and the solution added to the glycerol. The solution is then made up to the final volume with ethanol.

EXAMPLE 20

Ampoules

| | | |
|---|---|---|
| Ia | 9'-acetyl-10'-methyldigoxigenin-bis-digitoxoside | 0.050 mg. |
| | ethanol | 90.0 mg. |
| Ib | 9'-acetyl-10'-methyldigoxigenin-bis-digitoxoside | 0.250 mg. |
| | ethanol | 90.0 mg. |
| II | propylene glycol | 400.0 mg. |
| | water | ad 1.0 ml. |

Preparation: Separate solutions are made from Ia, Ib and II. Solution Ia respective Ib is intimately mixed with solution II and made up with water to the desired volume.

The activities of the novel compounds were determined and compared as follows: Two cats were used for each test, being intravenously injected with 30,50,100 or 200 µg/kg of a glycoside as set forth in the following table. The glycosides were labelled with tritium according to the method of Haberland and Maerten, German Published Specification 19 59 064-Digoxin according to V. Wartburg (Biochem. Pharmacol. 14, 1883 (1965)). In the 7 day test the radioactivities of the urine and feces were separately determined. In the table these excretion values are expressed in percent of the overall administred radioactivity.

The values of urine+feces after 2 days show the excretion rate; the separately determinded values for urine and feces after 7 days clarify the excretion way.

| Glycoside | 2 Day U + F | 7 Day U | 7 Day F | 7 Day U + F |
|---|---|---|---|---|
| Digitoxin | 7 | 10 | 54 | 64 |
| Digoxin | 51 | 39 | 38 | 77 |
| Digitoxigenin-bis-digitoxoside | 83 | 3 | 87 | 90 |
| 10'-Methyl-digitoxigenin-bis-digitoxoside (Ex. 2) | 64 | 9 | 67 | 76 |
| 10'-Methyl-digoxigenin-bis-digitoxoside (Ex. 10) | 62 | 23 | 67 | 90 |
| 9'-Methyl-digoxigenin-bis-digitoxoside (Ex. 9) | /** | 15 | 57 | 72 |

U = Urine
F = Feces
*Oral application
**not determined

It will be appreciated that the instant specification and examples are set forth by way of illustration and not limitation, and that various modifications and changes may be made without departing from the spirit and scope of the present invention.

We claim:

1. A cardenolide-bis-digitoxiside of the formula:

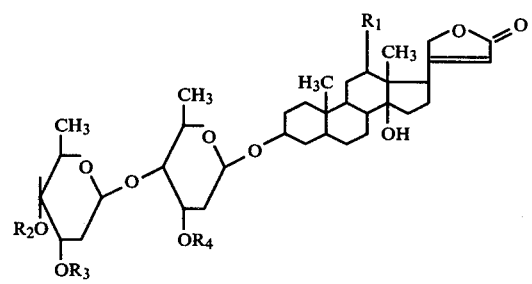

in which $R_1$ is a hydrogen atom, a hydroxyl group or an acyloxy radical containing up to 3 carbon atoms, and $R_2$, $R_3$ and $R_4$ each independently is a hydrogen atom or, an acyl or alkyl radical containing up to 3 carbon atoms, with the proviso that the compound contains at least one alkyl radical.

2. A compound according to claim 1, wherein such compound is 9'-methyldigitoxigenin-bis-digitoxoside.

3. A compound according to claim 1, wherein such compound is 10'-methyldigitoxigenin-bis-digitoxoside.

4. A compound according to claim 1, wherein such compound is 9'-methyldigoxigenin-bis-digitoxoside.

5. A compound according to claim 1, wherein such compound is 10'-methyldigoxigenin-bis-digitoxoside.

6. A cardioactive composition comprising a cardioactive effective amount of a compound according to claim 1 in admixture with a pharmacologically acceptable diluent.

7. A method for reducing the cardiac activity of a patient which comprises administering to such a patient a cardioactive effect amount of a compound according to claim 1.

8. The method according to claim 7, wherein such compound is
9'-methyldigitoxigenin-bis-digitoxoside,
10'-methyldigitoxigenin-bis-digitoxoside,
9'-methyldigoxigenin-bis-digitoxoside, or
10'-methyldigoxigenin-bis-digitoxoside.

* * * * *

UNITED STATES PATENT AND TRADEMARK OFFICE
CERTIFICATE OF CORRECTION

PATENT NO. : 4,353,895

DATED : October 12, 1982

INVENTOR(S) : Wolfgang Schaumann et al

It is certified that error appears in the above—identified patent and that said Letters Patent is hereby corrected as shown below:

Col. 1, lines 67, 68     Delete "bisdigitoxides" and insert --bisdigitoxoides--

Col. 2, beginning of 1st structure     Delete

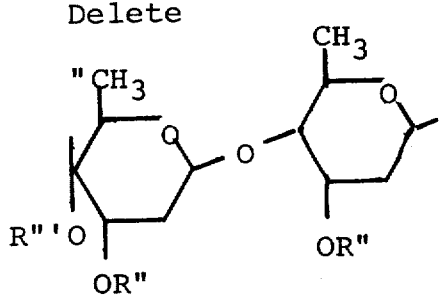

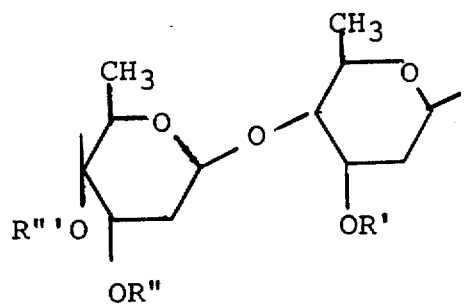

UNITED STATES PATENT AND TRADEMARK OFFICE
CERTIFICATE OF CORRECTION

PATENT NO. : 4,353,895

DATED : October 12, 1982

INVENTOR(S) : Wolfgang Schaumann et al

It is certified that error appears in the above—identified patent and that said Letters Patent is hereby corrected as shown below:

Col. 3, line 15      Delete "Arzneium" and insert --Arzneim--

Col. 6, line 25      Delete "30 mg" and insert --80 mg--

Signed and Sealed this

Twenty-eighth Day of December 1982

[SEAL]

Attest:

GERALD J. MOSSINGHOFF

Attesting Officer     Commissioner of Patents and Trademarks